United States Patent [19]

Bollag et al.

[11] 3,984,440
[45] Oct. 5, 1976

[54] POLYENE COMPOUNDS

[75] Inventors: Werner Bollag, Basel; Rudolf Ruegg, Bottmingen; Gottlieb Ryser, Basel, all of Switzerland

[73] Assignee: Hoffmann-La Roche Inc., Nutley, N.J.

[22] Filed: Aug. 7, 1974

[21] Appl. No.: 495,368

[30] Foreign Application Priority Data

Aug. 10, 1973 Switzerland............ 11559/73

[52] U.S. Cl............ 260/345.2; 260/247.1 B; 260/247.7 T; 260/247.7 R; 260/293.51; 260/293.58; 260/302 R; 260/302 H; 260/326.8; 260/345.5; 260/469; 260/247.7 Z; 260/471 R; 260/471 C; 260/473 F; 260/574; 260/575; 260/578; 260/577; 260/599; 260/606.5 F; 424/246; 424/248; 424/267; 424/283; 424/298; 424/300; 424/308; 424/333; 424/339; 424/343

[51] Int. Cl.² ............ C07D 311/02; C07D 311/72

[58] Field of Search............ 260/345.2; 260/345.5

[56] References Cited
UNITED STATES PATENTS 3,524,867  8/1970  Beal............ 260/345.2

OTHER PUBLICATIONS

Bass et al., Tetrahedron, 22, 265 (1966).
Korver et al., Tetrahedron, 22, 277 (1966).
Weedon et al., J. Chem. Soc., 2687 (1951).

*Primary Examiner*—James O. Thomas, Jr.
*Assistant Examiner*—Nicky Chan
*Attorney, Agent, or Firm*—Samuel L. Welt; Bernard S. Leon; R. Haine Swope

[57] ABSTRACT

Novel 9-substituted phenyl-3,7-dimethyl-nona-2,4,6,8-tetraenoic acid, -tetraenal or -tetraenol derivatives are described. The subject compounds are useful in the treatment of neoplasias, certain dermatoses and inflammatory and allergic dermatological conditions.

3 Claims, No Drawings

POLYENE COMPOUNDS

DETAILED DESCRIPTION OF THE INVENTION

The present invention pertains to compounds represented by the formula:

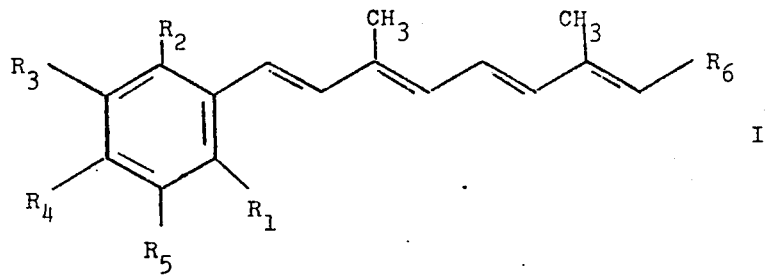

I wherein
- one adjacent pair of $R_1$ through $R_5$ is a trimethylene, tetramethylene, 1,3-butadienylene, oxytrimethylene or 3-oxypropenylene group which may be substituted with one or more lower alkyl groups and
- the remaining members of $R_1$ through $R_5$ each are selected from the group consisting of hydrogen, halogen, lower alkyl, lower alkenyl, lower alkoxy, lower alkenoxy, nitro, amino, mono(lower alkyl) amino, di(lower alkyl) amino and a nitrogen-containing heterocycle, at least one of said remaining members of $R_1$ through $R_5$ being other than hydrogen and
- $R_6$ is selected from the group consisting of formyl, hydroxymethyl, alkoxymethyl, alkanoyloxymethyl, carboxyl, alkoxycarbonyl, alkenoxycarboxyl, alkynoxycarbonyl, carbamoyl, mono(lower alkyl) carbamoyl di(lower alkyl)carbamoyl and a nitrogen containing heterocycle-substituted carbonyl group and pharmaceutically acceptable salts thereof.

The invention further pertains to compounds of the formulae:

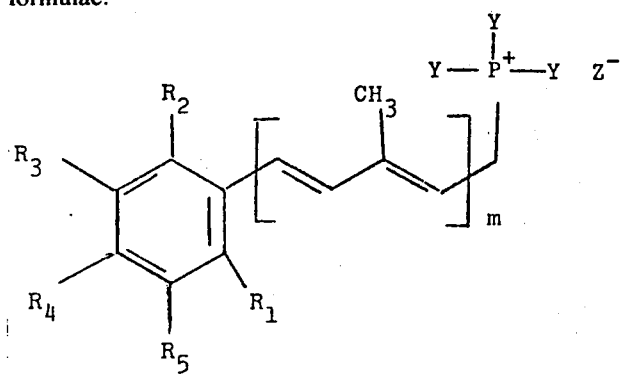

II(a)

and

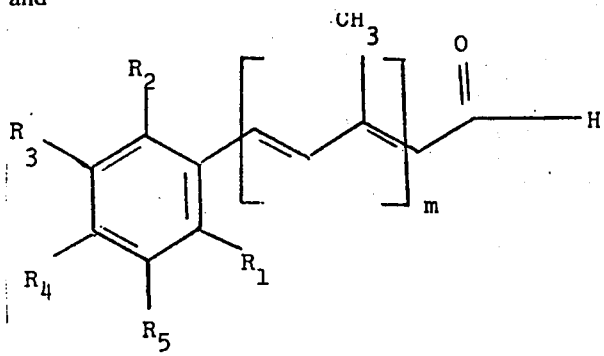

II(b)

wherein
- the meaning of $R_1$ through $R_5$ is as given above,
- Y is an aryl group,
- Z is an anion of an inorganic or organic acid and,
- m is zero or 1.

The term "halogen" as utilized in the instant specification denotes all form halogens, i.e., chlorine, bromine, iodine and fluorine, with chlorine and bromine being preferred. The terms "lower alkyl" and "lower alkenyl" denote both straight- and branched-chain groups containing 1 to 6 carbon atoms such as, for example, methyl, ethyl, isopropyl and 2-methylpropyl and vinyl, allyl and butenyl, respectively. The terms "lower alkoxy" and "lower alkenoxy" denotes groups containing 1 to 6 carbon atoms such as, for example, methoxy, ethoxy and isopropoxy and vinyloxy and allyloxy, respectively.

The amino group as represented in the above formulae may be mono- or disubstituted by lower alkyl groups containing from 1 to 6 carbon atoms such as, for example, methylamino, diethylamino and isopropylamino.

The terminology "nitrogen-containing herterocycle" as utilized herein denotes 5- or 6-membered ring containing a nitrogen atom and which may contain an additional hetero atom selected from the group consisting of oxygen, nitrogen and sulfur. Examples of preferred groups in accordance with the invention include pyrrolidino, piperidino, morpholino and thiomorpholino. The alkoxy portion of the alkoxymethylene and alkoxycarbonyl group in the above formulae are preferably straight- or branched- chain groups containing from one to six carbon atoms such as, for example, methoxy, ethoxy or isopropoxy. The alkoxy portion of said groups, however, may also contain from 7 to 20 carbon atoms. Of this group the cetyloxy group is preferred.

The alkenoxycarbonyl and alkynoxycarbonyl groups in the above formulae preferably contain 2 to 6 carbon atoms in the alkenoxy and alkynoxy portions, respectively. Examples of suitble groups include allyloxy and 2-propynyloxy. The alkanoyloxy portion of the alkanoyloxymethyl group of the above formula can be derived from lower alkanecarboxylic acids having from 1 to 20 carbon atoms, preferbly from 1 to 6 carbon atoms. Examples of suitable acids include acetic acid, propionic acid, pivalic acid, palmitic acid and stearic acid. The carbamoyl group of the above formulae can be mono- or di-substituted by straight- or branched- chain lower alkyl groups. Examples of suitable preferred groups include methylcarbamoyl, dimethylcarbamoyl and diethylcaramoyl. The nitrogen-containing heterocycle protion of the nitrogen-containing heterocycle-substituted carbonyl group is as defined above.

Preferred compounds of formula I in accordance with the invention include the following:
9-(4,6-dimethyl-indan-5-yl)-3,7-dimethyl-nona-2,4,6,8-tetraen-1-oic acid ethyl ester,
9-(8-methoxy-6,7-dimethyl-tetralin-5-yl)-3,7-dimethyl-nona-2,4,6,8-tetraen-1-oic acid,
9-(4-methoxy-2,3-dimethyl-naphthalen-5-yl)-3,7-dimethyl-nona-2,4,6,8-tetraen-1-oic acid ethyl ester,
9-(2,2,5,7,8-pentamethyl-chroman-6-yl)-3,7-dimethyl-nona-2,4,6,8-tetraen-1-oic acid and
9-(5,7,8-trimenthyl-chromen-6-yl)-3,7-dimethyl-nona-2,4,6,8-tetraen-1-oic acid methyl ester.

In accordance with the present invention, the novel polyene compounds of formula I are prepared by condensing a compound represented by the formula

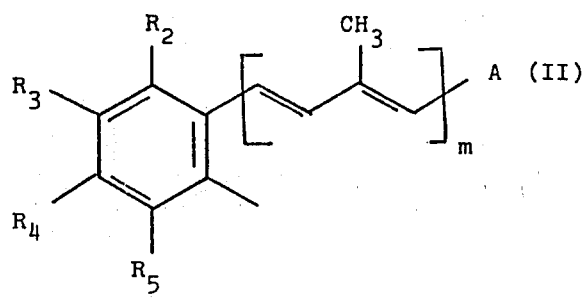

with a compound represented by the formula

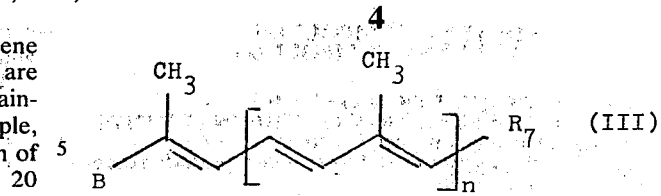

wherein $R_1$ through $R_5$ are as given above,
one member of A and B is formyl and the other is a triarylphosphoniummethyl group represented by the formula $-CH_2-P[Y]_3^+ Z^-$ wherein Y and Z have the meanings given above and,
wherein B is formyl,
$R_7$ is selected from the group consisting of alkoxymethyl, alkanoyloxymethyl, carboxy, alkoxycarbonyl alkenoxycarbonyl and alkynoxycarbonyl,
wherein B is triarylphosphonium-methyl,
$R_7$ is selected from the group consisting of formyl, dialkoxymethy, carboxyl, alkoxycarbonyl, alkenoxycarbonyl and allynoxycarbonyl and
one member of $m$ and $n$ is 1 and the other is zero.

Wherein a carboxylic acid is obtained, it may be esterified or amidated. Wherein an ester is formed, it may, if desired, be hydrolyzed or amidated. Wherein either a carboxylic acid or ester are obtained, these may optionally be reduced to form the corresponding alcohol. Such alcohols may be etherified or esterified. The alcohol can also, if desired, be saponified. The alcohol or an ester thereof can further be oxidized to form the corresponding carboxylic acid. An acid or amine obtained can, if desired, be transformed into a pharmaceutically acceptable salt.

The aryl groups represented by Y in the above formulae include all generally known aryl groups. Preferred groups include, for example, mononuclear groups such as phenyl, lower alkyl-substituted phenyl and lower alkoxy-substituted phenyl such as, for example, tolyl, xylyl, mesityl and p-methoxyphenyl. Preferred among the inorganic acid anions represented by Z in the above formulae are chlorine, bromide, iodide and hydrosulfate and, of the organic acid anions, the tosyloxy ion is preferred.

The novel compounds of formula II above wherein A is a triarylphosphonium-methyl groups, i.e. the compounds of formula II(a) can be prepared in the following manner. Wherein $m$ in formula II(a) is zero, a corresponding ($R_1-R_5$)-benzene is treated with formaldehyde in the presence of a hydrohalic acid such as, for example, concentrated hydrochloric acid in a solvent, preferably glacial acetic acid, and reacting the resulting ($R_1-R_5$)-benzyl halide in a conventional manner with a triarylphosphine, preferably triphenylphosphine, in a suitable organic solvent, preferably toluene or benzene.

An alkoxy group may be introduced into the ($R_1-R_5$)-benzene by, for example, alkylation of a hydroxy group. For example, the corresponding phenol can be reacted with an alkyl halide such as, for example, methyl iodide or with dimethyl sulfate preferably in the presence of a solvent such as an alkanol and a base, such as for example, potassium carbonate.

Compounds of formula II(a) wherein m is 1 are prepared by subjecting the corresponding ($R_1$–$R_5$)-benzene to formylation in the presence of a Lewis acid. Examples of suitable formylating agents include an orthoformic acid ester, formyl chloride and dimethylformamide. Preferred Lewis acids are the halides of zinc, aluminum, titanium, tin and iron such as, for example, zinc chloride, aluminium trichloride, titanium tetrachloride, tin tetrachloride and iron trichloride, as well as the halides of inorganic and organic acids such as, for example, phosphorus oxychloride, methanesulfonyl chloride and the like.

If the formylating agent is present in excess, the formylation may be carried out without the addition of an additional solvent. However, it is preferred to carry out the formylation in an inert solvent such as for example, nitrobenzene, a chlorinated hydrocarbon such as methylene chloride and the like. The reaction is carried out at a temperature between 0°C. and the boiling point of the mixture.

The ($R_1$–$R_5$)-benzaldehydes thus obtained are converted by conventional procedures, for example, by condensation with acetone in the cold, i.e. at a temperature from about 0°–30°C. in the presence of alkali, e.g. dilute aqueous sodium hydroxide to ($R_1$–$R_5$)-phenyl-but-3-en-2-one which is in turn converted by conventional procedures, e.g. an organometallic reaction such as a Grignard reaction with the addition of acetylene, to The corresponding ($R_1$–$R_5$)-phenyl-3-methyl-3-hydroxy-penta-4-en-1-yne. The resulting tertiary acetylene carbinol is then partially hydrogenated conventionally utilizing a partially deactivated noble metal catalyst, i.e. a Lindlar catalyst, to a tertiary ethylenic carbinol which is then converted to the desired phosphonium salt of formula II under allylic rearrangement by treatment with a triarylphosphine, preferably triphenylphospline, in the presence of a hydrogen halide such as, for example, hydrogen chloride or hydrogen bromide in a suitable solvent such as, for example benzene.

Compounds of formula II wherein A is a formyl group, i.e. compounds of formula II (b) wherein m is zero can be prepared by formylating a ($R_1$–$R_5$)-benzene as described above to directly obtain the corresponding ($R_1$–$R_5$)-benzaldehyde.

Compounds of formula II (b) wherein m is 1 can be prepared, for example, by submitting a ($R_1$–$R_5$)-phenyl-but-3-en-2-one such as described above to a Wittig reaction with ethoxycarbonyl-methylene-triphenylphosphorane. The resulting ($R_1$–$R_5$)-phenyl-3-methyl-penta-2,4-dien-1-oic acid ethyl ester is subsequently reduced in the cold with a mixed metal hydride, preferably lithium aluminum hydride in an organic solvent such as, for example, ether, tetrahydrofuran or the like, to form a ($R_1$–$R_5$)-phenyl-3-methyl-penta-2,4-dien-1-ol. This alcohol is then oxidized, e.g. by treatment with manganese dioxide in an organic solvent such as acetone or methylene chloride at a temperature between 0°C and the boiling point of the mixture to yield the desired ($R_1$–$R_5$)-phenyl-3-methyl-penta-2,4-dien-1-al.

The compounds of formula III are also, in part, novel.

The compounds of formula III wherein B is a triarylphosphonium-methyl group and N is zero can readily be prepared by reating 3-halomethyl-crotonic acid, which may be esterified or an etherified 3-halomethyl-crotyl alcohol with a triarylphosphine, preferably triphenyl-phosphine in a solvent, preferably toluene or benzene.

Compounds of formula III wherein B is a triarylphosphoniummethyl group and n is 1 can be prepared, for example, reducing the formyl group of the corresponding aldehyde of formula III to the hydroxymethyl group utilizing a metal hydride or alkyl metal hydride such as, for example, sodium borohydride, in an alkanol such as, for example, ethanol or isopropanol. The resulting alcohol can be conventionally halogenated utilizing, for example, phorphorus oxychloride and the resulting 8-halo-3,7-dimethyl-octa-2,4,6-triene-1-carboxylic acid, or a derivative thereof, reacted with a triarylphosphine, preferably triphenylphosphine, in a solvent such as, for example, toluene or benzene to yield the desired phosphonium salt of formula III.

Compounds of formula III wherein B is formyl and n is zero can be prepared by oxidatively cleaving, e.g. by lead tetraacetate at room temperature in an organic solvent such as benzene, tartaric acid which may be esterified if desired to yield a glyoxalic acid derivative which is conventionally condensed with propionaldehyde, preferably at an elevated temperature, i.e. 60°–110°C in the presence of an amine to yield with water cleavage the desired 2-formyl-crotonic acid derivative.

Compounds of formula III wherein B is formyl and $n$ is 1 can be prepared, for example, by reacting 4,4-dimethoxy-3-methyl-but-1-en-3-ol with phosgene in the cold, preferably at −10° to −20°C. in the presence of an amine such as, for example, pyridine and condensing the resulting 2-formyl-4-chloro-but-2-ene under the conditions of a Wittig reaction with 2-formyl-crotonic acid, optionally esterified, or a-formyl-crotyl alcohol, optionally esterified or etherified, to yield the desired aldehyde of formula III.

In accordance with the present invention, a phosphonium salt of formula II is condensed with an aldehyde of formula III or vice versa, the condenstion is carried out under conditions of a Wittig reaction, i.e. in the presence of an acid-binding agent such as, for example, an alkali metal alcholate such as sodium methylate or an alkylene oxide, preferably ethylene oxide or 1,2-butylene oxide, which may be alkyl substituted. The condensation may be carried out in a solvent, preferably a chlorinated hydro-carbon such as methylene chloride or dimethylformamide and at a temperature between room temperature and the boiling point of the mixture.

A carboxylic acid of formula I can be converted in a conventional manner, for example, by treatment with thionyl chloride, preferably in the presence of pyridine, into a acid chloride which can be converted into an amide by treatment with ammonia or into an ester by reaction with a suitable alkanol.

A carboxylic acid ester of formula I can be hydrolyzed to a carboxylic acid in a conventional manner such as, for example, by treatment with an alkali, preferably an aqueous-alcoholic solution of sodium hydroxide or potassium hydroxide at a temperature between room temperature and the boiling point of the mixture. The resulting carboxylic acid can then be amidated utilizing an acid halide as described above. Alternately, a carboxylic acid ester can be directly amidated as described hereinafter.

A carboxylic acid ester of formula I can be converted directly into the corresponding amide by treatment with lithium amide, preferably at room temperature.

A carboxylic acid or a carboxylic acid ester of formula I may be reduced to the corresponding alcohol in a conventional manner such as, for example, by treatment with a metal hydride or alkyl metal hydride in an inert solvent. Suitable hydrides include mixed metal hydrides such as lithium aluminum hydride and bis-[methoxy-ethylenoxy]-sodium aluminum hydride. Suitable inert solvents include, for example, ether, tetrahydrofuran and dioxane wherein lithium aluminum hydride is utilized and ether, hexane, benzene and toluene wherein diisobutyl-aluminum hydride or bis-[methyloxy-ethylenoxy]-sodium aluminum hydride are utilized.

An alcohol of formula I can be etherified with an alkyl halide, such as for, for example, ethyl iodide in the presence of a base, preferably sodium hydride and in an organic solvent such as, for example, dioxane, tetrahydrofuran, 1,2-dimethoxyethane, dimethyl-formamide and the like, or in the presence of an alkali metal alcoholate in an alkanol and at a temperature between 0°C and room temperature.

An alcohol of formula I can also be esterified by treatment with an alkanoyl halide or anhydride, preferably in the presence of a base such as, for example, pyridine or triethylamine at a temperature between room temperature and the boiling point of the mixture, An alcohol ester can be saponified by conventional procedure such as previously descrived in connection with the carboxylic acid esters.

An alcohol of formula I can be oxidized to corresponding acid by conventional means such as, for example, silver (I) oxide and an alkali in water or an organic solvent miscible with water at a temperature between room temperature and the boiling point of the mixture.

An amine of formula I forms acid addition salts. Preferred are salts of pharmaceutically acceptable inorganic acids such as, for example, hydrochloric acid, hydrobromic acid, sulfuric acid and the like and organic acids such as, for example, benzoic acid, acetic acid, citric acid, lactic acid and the like. A carboxylic acid forms salts with bases. Preferred are pharmaceutically acceptable salts such as the alkali metal salts, i.e. the sodium salt and the potassium salt.

The compounds of formula I can occur as a cis/trans mixture which may be separated by conventional procedures and isomerized to the all-trans compounds.

The polyene compounds of formula I are useful in the topical and systemic prophylaxis and treatment of benignant and malignant neoplasias and premalignant lesions. The tumor-inhibiting activity of the polyene compounds of the invention is significant. In the papilloma tests, tumors induced with dimethyl-benzanthracene and croton oil were shown to regress. The diameter of such papillomas in mice decreased by 55% within two weeks upon intraperitoneal administration of 400mg/kg/week of 9-(2,2,5,7,8-pentamethyl-chroman-6-yl)-3,7-dimethyl-nona-2,4,6,8-tetraen-1-oic acid.

The polyene compounds of formula I are further useful in the topical and systemic treatment of acne, psoriasis and other dermatoses accompanied by an increased or pathologically altered cornification and for the treatment of inflammatory and allergic dermatological conditions. The compounds of formula I can also be utilized in the treatment of conditions of the mucous membranes characterized by inflammatory, degenerative or metaplastic alterations.

The compounds of formula I may be administered enterally, parenterally or topically. The dosages will very according to mode of administration, the condition being treated and the requirements of the patient. For oral administration, from about 5 mg to about 200 mg of the compounds of formula I daily in one or more dosages are contemplated. A preferred oral dosage form is capsules containing from about 10 mg to about 100 mg of active ingredient or the equivalent amount of a pharmaceutically acceptable salt thereof. For topical administration, preferred dosage forms are solutions containing the active ingredient in from 0.01% by weight to about 0.3% by weight, preferably from about 0.02% by weight to about 0.1% by weight and ointments and creams containing from about 0.05% by weight to about 5% by weight, preferably from about 0.1% by weight to about 2.0% by weight active ingredient.

The toxicity of the compounds of formula I is slight. For example, as is evident from the following Table, the acute toxicity [$LD_{50}$] of 9-(2,2,5,7,8-pentamethyl-chroman-6-yl)-3,7-dimethyl-nona-2,4,6,8-tetraen-1-oic acid in mice after intraperitoneal administration in rape oil is 950 mg/kg.

TABLE

| Days Past | Acute Toxicity | | |
|---|---|---|---|
| Administration | $LD_{10}$ mg/kg | $LD_{50}$ mg/kg | $LD_{90}$ mg/kg |
| 1 | >4000 | >4000 | >4000 |
| 10 | 690 | 950 | 1300 |
| 20 | 690 | 950 | 1300 |

Wherein, in accordance with the present invention, the compounds of formula I are administered by either enteral of parenteral modes, suitable pharmaceutical dosage forms include tablets, capsules, dragees, syrups, suspensions, solutions, suppositories and the like for enteral administration. Parenteral dosage forms may be infusions or injectable solutions which can be injected intraveneously or intramuscularly. These preparations can contain other medicinally active substances as well as inert binding agents, fillers, carrier or diluents. Additional additives such as flavoring agents, preservatives, stabilizers, emulsifying agents, buffers and the like may be added in accordance with accepted practices of pharmaceutical compounding. It is preferred to incorporate into the preparations herein described one or a mixture of antioxidants recognized as being suitable for such preparations such as, for example, N-methyl-γ-tocopherol-amine, tocopherols, butylated hydroxyanisole, butylated hydroxytoluene, ethoxyquin and the like. The carriers and diluents utilized may be organic or inorganic substances such as, for example, water, gelation, lactose, starches, magnesium stearate, talc, gum arabic, polyalkyleneglycols and the like.

For topical administration, the polyene compounds of formula I are incorporated into ointments, tinctures, creams, solutions, lotions, sprays, suspensions and the like. Ointments, creams and solutions are preferred. These pharmaceutical preparations for topical administration can be prepared by mixing the polyene compounds, as the active ingredient, with non-toxic, inert solid or liquid carriers suitable for topical treatment in accordance with accepted pharmaceutical practices.

The following examples further illustrate the invention. All temperatures are in degrees centigrade.

EXAMPLE 1

A total of 60 g of 2,2,5,7,8-pentamethyl-chromane was introduced into 150 ml of glacial acetic acid and, after the addition of 280 ml of concentrated hydrochloric acid and 30 ml of a 35% aqueous formaldehyde solution, the mixture was stirred initially for 3 hours at 70°. An additional 10.5 ml of 35% formaldehyde was then added and the mixture stirred for a further 3 hours at 70°. The mixture was subsequently diluted with water and extracted with ether. The ether extract was washed successively with 0.3-N sodium hydroxide and water, dried over sodium sulfate and evaporated under reduced pressure. The residual 6-chloromethyl-2,2,5,7,8-pentamethyl-chromane melted at 75°–77°.

Twenty five grams of the thus-formed 6-chloromethyl-2,2,5,7,8-pentamethyl-chromane were dissolved in 50 ml of benzene. The solution was treated with 27 g of triphenylphosphine and stirred for 6 hours under reflux to form 2,2,5,7,8-pentamethyl-chroman-6-methyltriphenylphosphonium chloride as a precipitate which was used in the condensation described below without purification.

After the addition of a small amount of iron (III) nitrate, 2700 ml of liquid ammonia were treated portionwise, with stirring and cooling, with 169.5 g of potassium. As soon as the initially blue color disappeared (i.e. after about 30–45 minutes), acetylene gas was led through in a stream of 3 liters/minute until the dark color of the mixture lightened. The gas stream was then reduced to a flow of 2 liter/minute and the mixture treated dropwise with a solution of 500 g of methylglyoxal dimethylacetal in 425 ml of absolute ether. The flow with acetylene was continued with stirring for an additional hour. The mixture was subsequently treated portionwise with 425 g of ammonium chloride, gradually warmed to 30° within 12 hours (with evaporation of ammonia) and extracted with 1600 ml of ether. The ether extract was dried over sodium sulfate and evaporated under reduced pressure. After rectification, the residual 4,4-dimethoxy-3-methyl-but-1-yn-3-ol boiled at 33°/0.03 Torr; $n_D^{25}$ = 1.4480.

A total of 198 g of 4,4-dimethyl-but-1-yn-3-ol was dissolved in 960 ml of high-boiling petroleum ether and, after the addition of 19.3 g of 5% palladium catalyst and 19.3 g of quinoline, hydrogenated under normal conditions. After the uptake of 33.5 liters of hydrogen, the hydrogenation was discontinued. The catalyst was filtered off and the filtrate evaporated under reduced pressure. The residual 4,4-dimethoxy-3-methyl-but-1-en-3-ol boiled at 70°–72°/18 Torr after rectification.

A total of 195 ml of phosgene was led into 1570 ml of carbon /tetrachloride at −10°. After the addition of 213 g of pyridine, the solution was treated dropwise at a temperature of −10° to −20° with 327 g of 4,4-dimethoxy-3-methyl-but-1-en-3-ol. The mixture was slowly warmed with stirring to 25°, stirred for a further 3 hours at room temperature, cooled to 15° and treated with 895 ml of water. The aqueous phase which separated was discarded. After standing for 12 hours in the cold, the organic phase was treated with 448 ml of 5% sulfuric acid, stirred for 5 hours, with water, dried over sodium sulfate and evaporated under reduced pressure. After rectification, the residual 2-formyl-4-chloro-but-2-ene boiled at 37°–40°/1.8 Torr; $n_D^{25}$ = 1.4895.

A total of 165.7 g of 2-formyl-4-chloro-but-2-ene was dissolved in 840 ml of benzene and treated with 367 g of triphenyl-phosphine. The mixture was heated to boiling under nitrogen gas for 12 hours under reflux and then cooled 20°. The precipitated 2-formyl-but-2-ene-4-triphenylphosphonium chloride melted at 250°–252° after washing with benzene and drying.

A total 212.6 g of 2-formyl-but-2-ene-4-triphenylphosphonium chloride and 95 g of 3-formylcrotonic acid ethyl ester were introduced into 1100 ml of ethanol and treated at 5° with a solution of 57 g of triethylamine in 60ml of ethanol. The mixture was stirred for 6hours at 25°, cooled, introduced into water and thoroughly extracted with hexane. The hexane phase was washed repeatedly with methanol/water (6:4), then with water, dried over sodium sulfate and filtered. The filtrate was isomerised for 12 hours by shaking with iodine. The iodine was removed by adding sodium thiosulphate. The filtrate was again washed with water dried and evaporated under reduced pressure. The residual 7-formyl-3-methyl-octa-2,4,6-trien-1-oic acid ethyl ester boiled at 102°–103°/0.09 Torr after rectification.

A total of 52 g of 2,2,5,7,8-pentamethyl-chroman-6-methyl-triphenyl phosphonium chloride formed above was introduced under a nitrogen atmosphere into 30 ml of toluene and, after the addition of 30 ml of butylene oxide and 19.3 of the 7-formyl-2-methyl-octa-2,4,6-trien-1-oic acid ethyl ester previously formed the mixture was heated under reflux for 6 hours at 81°–85°. The resulting solution was taken up in hexane. The hexane extract was washed several times with methanol/water (70:30). The practically colorless extract was then evaporated under reduced pressure. The residual 9-(2,2,5,7,8-pentamethyl-chroman-6-yl) 3,7-dimethyl-nona-2,4,6,8-tetraen-1-oic acid ethyl ester melted clearly at 120°–122° after adsorption on 300 g of silicagel [eluant; hexane/ether (98:2)].

The residual ester was subsequently saponified by treatment with alcoholic potassium hydroxide. The hydrolysate was acidified with acetic acid, filtered an washed with water. The free acid was taken up in methylene chloride. The extract was then dried over sodium sulfate and evaporated under reduced pressure. The residual 9-(2,2,5,7,8-pentamethyl-chroman-6-yl)-3,7-dimethyl-nona-2,4,6,8-tetraene-1-oic acid melted at 216°–218° after recrystallization from methylene chloride.

EXAMPLE 2

Sixty two grams of 8-hydroxy-6,7-dimethyl-tetralin were introduced into 231 ml of methanol and, after the addition of 22.9 ml of water, treated, with stirring, with 30.8 g of solid potassium hydroxide. The solution, which became clear after some time, 78.5 g of methyl iodine were added dropwise over a period of 20 minutes at 0°–5°. The mixture was stirred for 2 hours at room temperature, heated under reflux conditions for 12 hours at 60°, treated with a further 10 g of potassium hydroxide and 26 g of methyl iodine and again heated for 12 hours at 60°. After cooling, the mixture was diluted with 1000 ml of water and thoroughly extracted with a total of 1500 ml of ether. The extract was washed successively with 3-N sodium hydroxide and water, dried over sodium sulfate and evaporated under reduced pressure. The residual 8-methoxy-6,7-dimethyl-tetralin boils in a high vacuum at 58°–59°/0.01 Torr after rectification.

A total of 41.5 g of 8-methoxy-6,7-tetralin was introduced into 104 ml of acetic acid and, after the addition of 192 ml of 37% hydrochloric acid and 18.9 g of 35% formaldehyde, stirred for 3 hours at 70°. The mixture was then treated with a further 7.26 of g or 35% formaldehyde, stirred again for 3 hours at 70°, subsequently cooled and extracted with 600 ml of benzene. The benzene extract was rinsed successively with an aqueous sodium carbonate solution and water, dried over sodium sulfate and evaporated under reduced pressure. The residual 5-chloromethyl-8-methoxy-6,7-dimethyl-tetralin melted at 80°–81° after recrystallisation from hexane.

Twenty seven grams of the thus-formed 5-chloromethyl-8-methoxy-6,7-dimethyl-tetraline were dissolved in 50 ml of benzene. The solution was treated with 29 g of triphenylphosphine and stirred under reflex for 6 hours. The precipitated 8-methoxy-6,7-dimethyl-tetralin-5-methyltriphenylphosphonium chloride was used in the condensation described below without further purification.

7-Formyl-3-methyl-octa-2,4,6-trien-1-oic acid butyl ester used in the condensation described below was prepared in an analogous manner to that described in Example 1 for the preparation of 7-formyl-3-methyl-octa-2,4,6-trien-1-oic acid ethyl ester. The butyl ester boiled at 102°–105°/0.09 Torr.

A total of 27 g of the 8-methoxy-6,7-dimethyl-tetralin-5-methyl triphenylphosphonium chloride formed above was introduced under a nitrogen atmosphere into 15 ml of toluene and, after the addition of 25 ml of butylene oxide and 25.6 g of 7-formyl-3-methyl-octa-2,4,6-trien-1-oic acid butyl ester, heated for 3 hours under reflux at 80°–81°. The solution was subsequently taken up in hexane and extracted with methanol/water (80:20). The extract was evaporated under reduced pressure and the residual 9-(8-methoxy-6,7-dimethyl-tetralin-5-yl)-3,7-dimethyl-nona-2,4,6,8-tetraen-1-oic acid butyl ester purified by adsorption on 600 g of silicagel [eluant: hexane/ether (98:2)]. The product was subsequently saponified by treatment with alcoholic potassium hydroxide. The hydrolysate was acidified with acetic acid, filtered and washed with water. The free acid was taken up in methylene chloride. The extract was then dried over sodium sulfate and evaporated under reduced pressure. The residual 9-(8-methoxy-6,7-dimethyl-tetralin-5-yl)-3,7-dimethyl-nona-2,4,6,8-tetraen-1-oic acid melted at 188°–190° after recrystallization from benzene.

EXAMPLE 3

A total of 17.7 g of 4-methoxy-2,3-dimethyl-naphthalene was introduced into 40 ml of glacial acetic acid and, after the addition of 74 ml of concentrated hydrochloric acid and 9 ml of 35% formaldehyde, heated at 70° with stirring for 1 hour. After the addition of an additional 2 ml of formaldehyde, the mixture was stirred for an hour at 70°, cooled, diluted with water and extracted with ether. The extract was washed successively with water and a saturated aqueous sodium bicarbonate solution, dried and evaporated. The residual 1-chloromethyl-4-methoxy-2,3-dimethyl-naphthalene melted at 93°–94°.

Twenty seven grams of the thus-formed 1-chloromethyl-4-methoxy-2,3-dimethyl-naphthalene were dissolved in 50 ml of benzene. The solution was treated with 24 g of triphenyl-phosphine and heated under reflux for 6 hours. The precipitated 4-methoxy-2,3-dimethyl-naphthalene-1-methyltriphenylphosphonium chloride was used in the condensation described below without further purification.

A total of 21 g of 4-methoxy-2,3-dimethyl-naphthalene-1-methyl-triphenylphosphonium chloride formed above was introduced under a nitrogen atmosphere into 15 ml of toluene and, after the addition of 35 ml of butylene oxide and 19 g of 7-formyl-3-methyl-octa-2,4,6-trien-1-oic acid ethyl ester, heated for 2 hours under reflux at 80°–81°. The solution was then extracted with petroleum ether (boiling range 80°–110°). The extract was washed with methanol/water (70:30), dried and evaporated under reduced pressure. The residual 9-(4-methoxy-2,3-dimethyl-naphthalen-1-yl)-3,7-dimethyl-nona-2,4,6,8-tetraen-1-oic acid ethyl ester thus formed was purified by adsorption on 500 g of silicagel (eluant: benzene). The ester melted at 90°–92° after recrystallization from hexane.

EXAMPLE 4

Soft gelatin capsules were filled with the following composition:

| Ingredient | Amount in mg |
| --- | --- |
| 9-(2,2,5,7,8-Pentamethyl-chroman-6-yl)-3,7-dimethyl-nona-2,4,6,8-tetraen-1-oic acid | 10.0 |
| Wax mixture | 41.5 |
| Vegetable oil | 98.0 |
| Trisodium salt of ethylenediamine-tetraacetic acid | 0.5 |
| | 150.0 |

EXAMPLE 5

An ointment containing 0.3% of active ingredient was prepared in a conventional manner from following composition:

| Ingredient | Amount in Grams |
| --- | --- |
| 9-(4-Methoxy-2,3-dimethyl-naphth-1-yl)-3,7-dimethyl-nona-2,4,6,8-tetraen-1-oic acid ethyl ester | 0.3 |
| Cetyl alcohol | 2.7 |
| Lanolin | 6.0 |
| White petroleum jelly | 15.0 |
| Distilled Water q.s. ad | 100.0 |

EXAMPLE 6

A water/fat emulsion containing 0.3% of active ingredient was prepared by conventional procedure from the following composition:

| Ingredient | Amount in Grams |
| --- | --- |
| 9-(8-Methoxy-6,7-dimethyl-tetralin-5-yl)-3,7-dimethyl-nona-2,4,6,8-tetraen-1-oic acid | 0.3 |
| Magnesium stearate | 2.0 |
| Perhydrosqualene | 13.0 |
| Distilled Water q.s. ad | 100.0 |

We claim as our invention:

1. A compound having all trans configuration selected from compounds represented by the formula

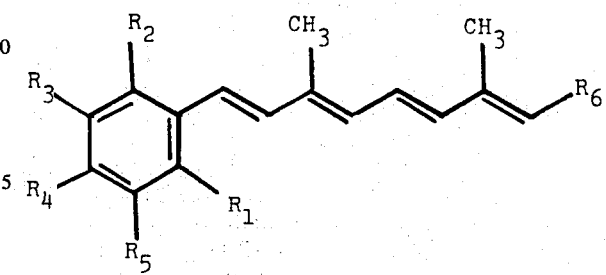

wherein one adjacent pair of $R_1$ through $R_5$ is a oxytrimethylene or 3-oxypropenylene group which may be substituted with one or two lower alkyl groups and the remaining members of $R_1$ through $R_5$ each are selected from the group consisting of hydrogen, lower alkyl and lower alkoxy, at least one of said remaining members of $R_1$ through $R_5$ being other than hydrogen and $R_6$ is selected from the group consisting of carboxyl and lower alkoxycarbonyl.

2. A compound in accordance with claim 1 wherein said compound is 9-(2,2,5,7,8-pentamethyl-chroman-6-yl)-3,7-dimethyl-nona-2,4,6,8-tetraen-1-oic acid ethyl ester.

3. A compound in accordance with claim 1 wherein said compound is 9-(2,2,5,7,8-pentamethyl-chroman-6-yl)-3,7-dimethyl-nona-2,4,6,8-tetraen-1-oic acid.

* * * * *